United States Patent

Sato et al.

[11] 4,238,423
[45] Dec. 9, 1980

[54] PROCESS FOR PREPARING CYCLO-1,3,2-OXAZAPHOSPHORYL DERIVATIVES

[75] Inventors: Tadao Sato; Hiraki Ueda; Kazuyuki Nakagawa, all of Tokushima, Japan

[73] Assignee: Otsuka Pharmaceutical Co., Ltd., Tokyo, Japan

[21] Appl. No.: 91,786

[22] Filed: Nov. 6, 1979

[30] Foreign Application Priority Data

Nov. 7, 1978 [JP] Japan .................. 53/137685

[51] Int. Cl.³ ............................. C07F 9/24
[52] U.S. Cl. .................. 260/968; 260/936
[58] Field of Search .............. 260/936, 968

[56] References Cited
FOREIGN PATENT DOCUMENTS
2644905 4/1977 Fed. Rep. of Germany .......... 260/936

*Primary Examiner*—Anton H. Sutto
*Attorney, Agent, or Firm*—Finnegan, Henderson, Farabow, Garrett & Dunner

[57] ABSTRACT

A novel process for preparing cyclo-1,3,2-oxazaphosphoryl derivatives represented by the formula (II),

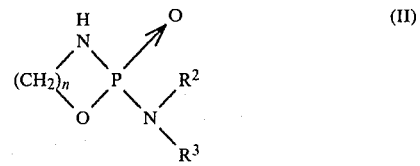

wherein $R^2$ and $R^3$ are respectively a lower alkyl group which may have halogen atom(s) or lower alkane-sulfonyloxy group(s) as substituted group(s) and n is an integer of 2 to 6, by acid cleaving the $R^1$—N bond of the compound represented by the formula (I),

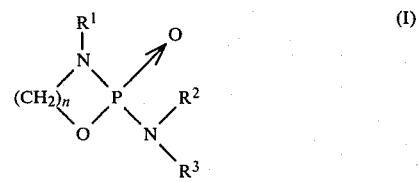

wherein $R^1$ is an α-arylalkyl group, by using a strong acid, the compound represented by the formula (II) being effective as an anticancer agent.

5 Claims, No Drawings

PROCESS FOR PREPARING CYCLO-1,3,2-OXAZAPHOSPHORYL DERIVATIVES

The present invention relates to a novel process for preparing cyclo-1,3,2-oxazaphosphoryl derivatives. More particularly the present invention relates to a novel process for preparing cyclo-1,3,2-oxazophosphoryl derivatives represented by the formula (II),

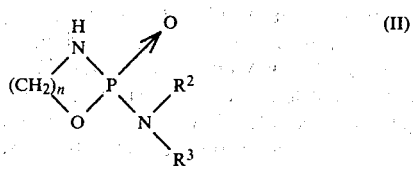

wherein $R^2$ and $R^3$ are respectively a lower alkyl group which may have halogen atom(s) or lower alkanesulfonyloxy group(s) as substituted group(s), and n stands for an integer of 2 to 6, by acid-cleaving the N—$R^1$ bond of 3-(α-arylalkyl)-cyclo-1,3,2-oxazaphosphoryl derivatives represented by the formula (I),

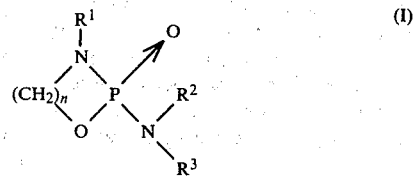

wherein $R^1$ stands for an α-arylalkyl group, and $R^2$, $R^3$ and n are the same as defined above.

Heretofore, as for a process for preparing cyclophosphamide by cleaving N—$R^1$ bond of the compound represented by the formula

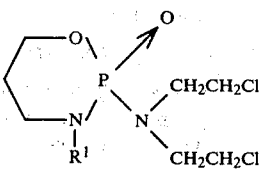

wherein $R^1$ stands for an α-arylalkyl group, a hydrogenation method (catalytic reduction method) has been known [cf.: R. Kinas, K. Pankiewicz and W. J. Stec,: Bull. Acad, Polon, Sci., 23, 981 (1975) and West German laid-open patent application No. 2644905].

However, the above mentioned known method has defects such that the method necessities an expensive catalyst for catalytic reduction, requires an extensive length of reaction time such as 10 hours or longer, and also requires a relatively high reaction temperature such as 50° C. or higher, which induces the decomposition of a relatively unstable cyclophosphamide once formed to result in a low yield of the desired compound.

The present inventors have made an extensive studies for finding a method for preparing the compound of the formula (II) which would be carried out easily and under more mild condition without incurring such defects of the prior arts. As the results of the studies, the present inventors have now found out a novel method for preparing the compound of formula (II), the method being carried out by cleaving the N—$R^1$ bond of the compounds of the formula (I) in a relatively shorter reaction time and at a lower reaction temperature by using an acid. This leads to the accomplishment of the present invention on the basis of such the new knowledge of the cleavage method of N—$R^1$ bond.

The starting compound of the formula (I) is either a known compound or a compound readily prepared according to any known method.

For example, a compound of the general formula (I) can easily be prepared through the following reaction scheme:

$R^1NH_2 + X(CH_2)_n—OH \longrightarrow$ (IV)    (V)

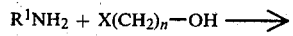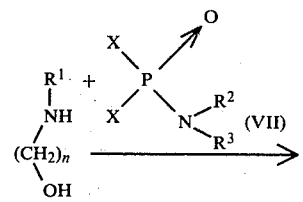

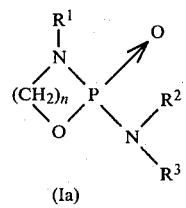

(Ia)

wherein $R^1$, $R^2$ and $R^3$ are the same as defined above, and X is a halogen atom.

A compound represented by the general formula (Ia) as prepared by the above process can easily be isolated into an optical isomer form of the general formula (Ib), if necessary.

The α-arylalkyl group as shown as $R^1$ herein is exemplified as α-arylalkyl group having a straight or branched chain alkyl group having 1 to 6 carbon atoms, such as benzyl, α-phenylethyl, α-phenylpropyl, α-phenylbutyl, α-phenylhexyl, α-naphtylmethyl, β-naphthylmethyl, α-(α-naphthyl)ethyl, α-(β-naphthyl)-ethyl or the like.

An electron donative substituent may be replaced on the aryl ring of the α-arylalkyl group. Said substituent may be, for example, a halogen atom, a lower alkyl group, a lower alkoxy group or a hydroxy group. Furthermore, said α-arylalkyl group having an asymmetric carbon atom, may be of optical isomer or racemate. The halogen atom may be fluorine, chlorine, bromine, or iodine atom. As for the lower alkanesulfonyloxy group, an alkanesulfonyloxy group having a straight or branched alkyl group having 1 to 6 carbon atoms is exemplified, such as methanesulfonyloxy, ethanesulfonyloxy, propanesulfonyloxy, isopropanesulfonyloxy, butanesulfonyloxy, tert-butanesulfonyloxy and hexanesulfonyloxy or the like. As for the lower alkyl group, a straight or branched alkyl group may be exemplified, such as methyl, ethyl, propyl, isopropyl, butyl, tert-butyl, hexyl group or the like. As for the lower alkoxy group a straight or branched chain alkoxy group having 1 to 6 carbon atoms is exemplified, such as methoxy, ethoxy, propoxy, isopropoxy, butoxy, tert-butoxy, hexyloxy or the like.

As for the lower alkyl group shown as $R^2$ or $R^3$, which may have a halogen atom or lower alkanesulfonyl group as a substituent, the followings are exemplified: for example, lower alkyl group as mentioned above, 2-chloroethyl, 3-chloropropyl, 4-chlorobutyl, 6-chlorohexyl, 2-bromoethyl, 2-fluoroethyl, 2-chloropropyl, 2,2-dimethyl-2-chloroethyl, 2-methanesulfonyloxyethyl, 3-methanesulfonyloxypropyl, 4-ethanesulfonyloxybutyl, 6-methanesulfonloxyhexyl, 4-butanesulfonyloxybutyl group or the like.

As for the starting material represented by the above general formula (I) either compound in optical isomer form or racemate form can be used. Especially when using the compound in optical isomer form, there is no racemization occurred in the course of the reaction of the present invention.

The process of the present invention can be carried out in the absence or presence of a solvent. As for the solvent usable in the present invention, water, a lower fatty acid such as formic acid, acetic acid, propionic acid or the like, an aromatic hydrocarbon such as benzene, toluene, xylene or the like, a saturated hydrocarbon such as n-hexane, cyclohexane, isooctane, or the like, an ether such as diethylether, 1,2-dimethoxyethane, anisole, or the like, and a halogenated hydrocarbon such as methylene chloride, 1,2-dichloroethane or the like can be exemplified. As for the acid usable in the invention, sulfuric acid, fluorosulfuric acid, trifluoroacetic acid, perchloric acid, hydrogen bromide, methanesulfuric acid, trifluoromethanesulfonic acid or the like can be exemplified. Among those acid, sulfuric acid, trifluoroacetic acid, hydrogen bromide trifluoromethanesulfonic acid and fluorosulfuric acid are preferred, and sulfuric acid having a concentration of 70% or higher is especially preferred. Those acid can be used in an amount from catalytic amount to large excess amounts, and ordinarily equimolar amount to about 20 times of molar quantity of the compound of the general formula (I) are preferably used.

The reaction of the present invention is carried out at a temperature of $-30°$ to $50°$ C., preferably at $-15°$ C. to a room temperature and for 1 minute to 1 hour, ordinarily for 5 to 30 minutes. The present invention is characterized in carrying out the reaction under such a moderate condition.

In the case of using sulfuric acid as the acid in the present invention, an inorganic acid salt such as ammonium sulfate or sodium sulfate may be added to the reaction system, and thereby the coloring of the reaction product can be avoided and improvement of yield can be attained.

The objective compound of the formula (I) can be easily purified after the reaction by using a conventional separation method, for example dilution with solvent, solvent extraction or recrystallization or the like.

The compound represented by the formula (II) obtained by the process of the present invention is a known compound and is useful as an anticancer agent. For example, $(\pm)$-cyclophosphamide has been used as anticancer agent and $S(-)$-cyclophosphamide and $R(+)$-cyclophosphamide have been known to have anti-cancer activity [P. J. Cox, et al.: Biochemical Pharmacology, 25, 993–996 (1976), Pergamon Press, printed in Great Britain].

The present invention can be illustrated by way of the following referential examples and examples.

REFERENTIAL EXAMPLE 1

A mixture of 14.1 g of $\gamma$-chloropropanol and 24.2 g of $S(-)$-phenylethylamine [having $[\alpha]_D^{25} = -37.4°$ (without solvent, optical purity=91%)]was heated on a oil bath at $120°$ C. for 15 hours. After cooling of the reaction mixture, thus obtained syrup-like oily substance was dissolved in a small amount of water, then 30% NaOH aqueous solution was added to obtain an amine in the free form from hydrochloride thereof. The water layer was extracted with chloroform and the chloroform layer was dried with anhydrous $MgSO_4$. After the chlorofm was removed by distillation, 17.2 g of a colorless liquid was obtained. B.p. $115°$–$118°$ C./1.2 mmHg, $[\alpha]_D^{25} \times -40.3°$ (c=6.6; in benzene). The obtained product was identified as $(S)$-$(-)$-$\gamma$-hydroxypropyl-$\alpha$-phenylethylamine by the methods of $^1H$-NMR and of mass-spectroscopy. Molecularion m/e=179 (1%).

A mixture of 8.95 g of $(S)$-$(-)$-$\gamma$-hydroxy-propyl-$\alpha$-phenylethylamine, 12.85 g of N-bis-($\beta$-chloroethyl)-aminodichlorophosphate and 12.1 g of triethylamine in 250 ml of benzene was stirred at a room temperature for 24 hours. Triethylamine hydrochloride was filtered out and the filtrate was concentrated by evaporation. The crude product was separated by column chromatography [silica gel=100–200 mesh, eluting agent=benzene/chloroform/acetone=8:2:1, $R_f$=0.28 (substance A) and $R_f$=0.20 (substance B) were separated]. The existence of the substances A and B in the respective fractions were determined by thin layer chromatography, at which the chromatogram was developed by iodine vapor.

Substance A: 2(S)-(2)-[bis(2-chloroethyl)amino]-3-[(S)-$\alpha$-phenylethyl]tetrahydro-2H-1,3,2-oxazaphosphorin 2-oxide in the form of colorless oily substance, yield: 5.2 g, $[\alpha]_D^{25}$: -62.4° (c=5.7, in benzene).

Substance B: 2(R)-(2)-[bis(2-chloroethyl)amino]-3-[(S)-$\alpha$-phenylethyl]tetrahydro-2H-1,3,2-oxazaphosphorin 2-oxide in the form of sirup-like liquid, yield: 4.1 g, $[\alpha]_D^{25}$=-1.6° (c=4.8, in benzene).

REFERENTIAL EXAMPLE 2

A method similar to that in Referential example 1, by using $R$-$(+)$-$\alpha$-phenylethylamine in place of $S$-$(-)$-$\alpha$-phenylethylamine, the following substances were obtained.

2(R)-2-[bis(2-chloroethyl)amino]-3-[(R)-phenylethyl]tetrahydro-2H-1,3,2-oxazaphosphorin 2-oxide in the form of an oily substance. $[\alpha]_D^{25}$=+63.4° (c=5.6 in benzene).

2(S)-2-[bis(2-chloroethyl)amino]-3-[(R)-phenylethyl]-tetrahydro-2H-1,3,2-oxazaphosphorin 2-oxide in the form of an oily substance. $[\alpha]_D^{25}$=-1.4° (c=4.5 in benzene).

EXAMPLE 1

2 Grams of ammonium sulfate was dissolved in 8 ml of concentrated sulfuric acid, then 2.5 g of 2(R)-2-[bis(2-chloroethyl)amino]-3-[(R)-$\alpha$-phenylethyl]-tetrahydro-2H-1,3,2-oxazaphosphorine 2-oxide was added under agitation and the mixture was stirred for 5 minutes. The reaction mixture was added to 20 ml of ice water and the mixture was extracted with n-hexane. The aqueous layer was extracted with trichloromethane. The trichloromethane layer was dried with anhydrous magnesium sulfate and the solvent was distilled off to obtain the crude crystals of $S(-)$-cyclophosphamide. The crystals were recrystallized from either to obtain S(−)-cyclophosphamide in colorless prism-like crystals.
Yield: 1.6 g (89%)
M.p.: 67°–68.5° C.
$[\alpha]_D^{25}$: −2.31° (c=8.9 in methanol)

EXAMPLE 2

25 Grams of 2(S)-2-[bis(2-chloroethyl)amino]-3-[(S)-α-phenylethyl]tetrahydro-2H-1,3,2-oxazaphosphorine 2-oxide was dissolved in 125 ml of anisol to obtain a solution. Then 25 ml of concentrated sulfuric acid was added to the solution dropwise with stirring under ice-cooling. The stiring was continued for further 15 minutes at the same temperature. Then, the reaction mixture was poured into 200 ml of ice-water and the same treatment as in Example 1 was carried out to obtain 15 grams (yield 85%) of R(+)-cyclophosphamide crystals in colorless prism-like form.
M.P.: 67°–68.5° C.
$[\alpha]_D^{25}$: +2.30° (C=8.5 in methanol)

EXAMPLE 3

3 Grams of 2(R)-2-[bis(2-chloroethyl)amino]-3-[(R)-α-phenylethyl]tetrahydro-2H-1,3,2-oxazaphosphorine 2-oxide was added to 15 ml of acetic acid being saturated with hydrogen bromide at room temperature and agitation was continued at the same temperature for 15 minutes. The reaction mixture was poured into 20 ml of ice water and the mixture was treated by the same manner as in Example 1 to obtain S(−)-cyclophosphamide.
Yield: 1.8 g (84%)
M.p.: 67°–68.5° C.
$[\alpha]_D^{25}$: -2.30° (C=8.8, in methanol)

EXAMPLE 4

2 Grams of ammonium sulfate was dissolved in 8 ml of concentrated sulfuric acid, then 2.8 grams of 2(R)-2-[bis(2-chloroethyl)amino]-3-[(R)-α-(p-chlorophenyl)-ethyl]tetrahydro-2H-1,3,2-oxazaphosphorine 2-oxide was added to the sulfuric acid solution under ice-cooling with stirring for 10 minutes. The reaction mixture was then treated by the same manner as in Example 1 to obtain S(−)-cyclophosphamide crystals in colorless prism form.
Yield: 1.5 g (83%)
M.p.: 67°–68.5° C.
$[\alpha]_D^{25}$: −2.32° (C=9.0, in methanol)

EXAMPLE 5

2 Grams of ammonium sulfate was dissolved in 8 ml of concentrated sulfuric acid, then 2.8 grams of 2(R)-2-[bis(2-chloroethyl)amino]-3-[(R)-α-(α-naphthyl)-ethyl]-tetrahydro-2H-1,3,2-oxazaphosphorine 2-oxide was added under ice-cooling with stirring for 10 minutes. The reaction mixture was treated by the same manner as in Example 1 and obtained S-(−)-cyclophosphamide crystals in colorless prism form.
Yield: 1.5 g (85%)
M.p.: 67°–68.5° C.
$[\alpha]_D^{25}$: −2.31° (C=0.91 in methanol)

EXAMPLES 6–10

According to Example 1, such compounds of the general formula (II) as shown in Table were obtained.

TABLE

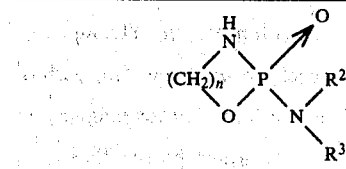

(II)

| Example No. | $-N\begin{smallmatrix}R^2\\R^3\end{smallmatrix}$ | n | Form of optical isomer | Physical properties |
|---|---|---|---|---|
| 6 | —N(CH₂CH₂Cl)₂ | 3 | Racemate | Monohydrate colorless crystals m.p. 41–45° C. |
| 7 | —N(CH₂CH₂Cl)₂ | 2 | Racemate | Colorless crystals m.p. 99.4° C. |
| 8 | —N(CH₂CH₂Cl)₂ | 4 | Racemate | Colorless crystals m.p. 76–77° C. |
| 9 | —N(CH₂CH₂Cl)₂ | 5 | Racemate | Oily substance Elemental analysis for C₉H₁₉O₂N₂Cl₂P |
| | | | C (%) | H (%) | N (%) |
| | Calculated: | | 37.39 | 6.62 | 9.69 |
| | Found: | | 37.52 | 6.78 | 9.81 |
| 10 | —N(CH₂CH₂Cl)₂ | 6 | Racemate | Oily substance Elemental analysis for C₁₀H₂₁O₂N₂Cl₂P |
| | | | C (%) | H (%) | N (%) |
| | Calculated: | | 39.62 | 6.98 | 9.24 |
| | Found: | | 39.85 | 7.19 | 9.41 |

EXAMPLE 11

2.7 Grams of 2(S)-2-[bis(2-chloroethyl)amino]-3-[(S)-(1-phenyl-2-p-toluyl)ethyl]tetrahydro-2H-1,3,2-oxazaphosphorine 2-oxide was dissolved in 50 ml of toluene. Then 3 ml of concentrated sulfuric acid was added dropwise to the obtained toluene solution with stirring under ice-cooling and the reaction was continued at the same temperature for 5 minutes. 50 Milliliters of petroleum ether was added to the reaction mixture and the obtained mixture was extracted with water. The water layer was extracted with chloroform. After drying the chloroform layer with anhydrous magnesium sulfate, chloroform was removed by distillation to obtain R(+)-cyclophosphamide in the yield of 1.5 gram (crude yield: 97%). The crude R(+)-cyclophosphamide was recrystallized from a mixture of ethylacetate and diisopropyl ether, the pure product of R(+)-cyclophosphamide was obtained in the yield of 1.35 g (87.1%) in the form of colorless prism-like crystals.
M.p.: 67°–68.5° C.
$[\alpha]_D^{20}$: +2.45° (C=10 in methanol)

EXAMPLE 12

According to a method similar to as in Example 11, 3 g of 2(R)-2-[bis(2-chloroethyl)amino]-3-[(R)-α-(α-naphthylethyl)]tetrahydro-2H-1,3,2-oxazaphosphorine 2-oxide was reacted and treated and 1.4 g of S(−)-cyclophosphamide was obtained.
M.p.: 67°–68° C.
$[\alpha]_D^{20}$: −2.37° (C=10 in methanol)

EXAMPLE 13

2 Grams of ammonium sulfate was dissolved in 8 ml of trifluoroacetic acid, then 2.5 g of 2(R)-2-[bis(2-chloroethyl)amino]-3-[(R)-α-phenylethyl]tetrahydro-2H-1,3,2-oxazaphosphorin 2-oxide was added under agitation and the mixture was stirred for 5 minutes. The reaction mixture was added to 20 ml of ice-water and the mixture was extracted with n-hexane. The aqueous layer was extracted with trichloromethane. The trichloromethane layer was dried with anhydrous magnesium sulfate and the solvent was removed by distillation to obtain crude crystals of S(−)-cyclophosphamide. The crystals were recrystallized from ether to obtain S(−)-cyclophosphamide in colorless prism-like crystals.

Yield: 1.5 g (84%)

M.p.: 67°–68.5° C.

$[\alpha]_D^{25}$: −2.38° (C=9.0 (in methanol))

EXAMPLE 14

25 Grams of 2(S)-2-[bis(2-chloroethyl)amino]-3-[(S)-α-phenylethyl]tetrahydro-2H-1,3,2-oxazaphosphorin 2-oxide was dissolved in 125 ml of anisol to obtain a solution. Then 30 ml of trifluoromethanesulfonic acid was added to the solution dropwise with stirring under ice-cooling. The stirring was continued for further 15 minutes at the same temperature. Then the reaction mixture was poured into 200 ml of ice-water and the same treatment as in Example 1 was carried out to obtain 16.5 g (yield: 92%) of R(+)-cyclophosphamide crystals in colorless prism-like form.

M.p.: 67°–68.5° C.

$[\alpha]_D^{25}$: +2.36° (C=9.2 in methanol). What we claim is:

1. Process for preparing cyclo-1,3,2-oxazaphosphoryl derivatives represented by the formula (II)

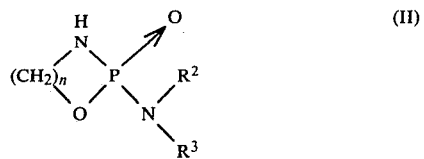

wherein $R^2$ and $R^3$ are respectively lower alkyl group which may have hologen atom(s) or lower alkansulfonyloxy group(s) as substituent(s), and n is an integer of 2 to 6, which comprises acid-cleaving the N—$R^1$ bond of 3(α-arylalkyl)-cyclo-1,3,2-oxazaphosphoryl derivatives represented by the formula (I)

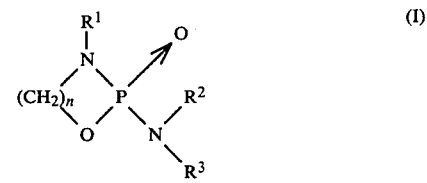

wherein $R^1$ signifies an α-arylalkly group and $R^2$, $R^3$, and n are the same as defined above, in the use of an acid selected from the group consisting of sulfuric acid, fluorosulfuric acid, trifluoroacetic acid, perchloric acid, hydrogen bromide, methanesulfonic acid, and trifluoromethanesulfonic acid.

2. Process according to claim 1, wherein said acid is one selected from the group consisting of sulfuric acid having a concentration of 75 percent by weight or higher, trifluoromethanesulfonic acid and hydrogen bromide.

3. Process according to claim 1, wherein the acid is used in an amount of equimolecular to 20 times of molar quantities of the compound represented by the formula (I) in said acid-cleaving reaction.

4. Process according to claim 1, wherein said acid-cleaving reaction is carried out at a temperature of −30° to 50° C., preferably −15° to room temperature.

5. Process according to claim 5, wherein said acid-cleaving reaction is carried out for a reaction time of 1 minute to 1 hour, preferably 5 to 30 minutes.

* * * * *